United States Patent [19]
Wong et al.

[11] Patent Number: 5,919,673
[45] Date of Patent: Jul. 6, 1999

[54] ONE-POT ENZYMATIC SULFATION PROCESS USING 3'-PHOSPHOADENOSINE-5'-PHOSPHOSULFATE AND RECYCLED PHOSPHORYLATED ADENOSINE INTERMEDIATES

[75] Inventors: Chi-Huey Wong, Rancho Sante Fe; Chun-Hung Lin, San Diego; Gwo-Jenn Shen, Carlsbad, all of Calif.

[73] Assignee: The Scripps Research Institute, LaJolla, Calif.

[21] Appl. No.: 08/408,774

[22] Filed: Mar. 22, 1995

[51] Int. Cl.[6] .............. C12P 11/00; C12P 33/00; C12P 19/04; C12P 19/32
[52] U.S. Cl. .............. 435/130; 435/101; 435/52; 435/92
[58] Field of Search .................. 435/130, 101, 435/52, 92

[56] References Cited

U.S. PATENT DOCUMENTS 5,376,535   12/1994   Onda et al. ................. 435/92

OTHER PUBLICATIONS

Brunngraber, J. Biol. Chem. 233(2):472–477 (1958).
Kopp et al, J. Biol. Chem. 247(11):3564–3570 (1972).
Varki, *Glycobiology*, 3:97 (1993).
Yuen et al., *J. Biol. Chem.*, 269:1595 (1994).
Hemmerich et al., *Biochemistry*, 33:4830 (1994).
Varki, *Proc. Natl. Acad. Sci.*, 91:7390 (1994).
van Boeckel et al., *Angew. Chem. Int. Ed. Eng.*, 32:1671 (1993).
Bernstein et al., *J. Biol. Chem.*, 199:745 (1952).
Robbins et al., *J. Biol. Chem.*, 233:686 (1958).
[EC 2.8.2.1–28] listed in *Enzyme Nomenclature 1992*, E. C. Webb, ed., Academic Press, San Diego, CA 1992, pp. 299–303.
Baddiley et al., *J. Am. Chem. Soc.*, 1067 (1957).
Cherniak et al., *J. Biol. Chem.*, 239:2986 (1964).
Sekura, *Methods in Enzymology*, 77:413 (1981).
Horwitz et al., *Biochem. Biophy. Acta.*, 480:376 (1977).
Satishchandran et al., *J. Biol. Chem.*, 264:15012 (1989).
Fernando et al., *Biosci. Biotech. Biochem.*, 57:1974 (1993).
Mukai, *Agric. Biol. Chem.* 53:883 (1989).
Leyh et al., *J. Biol. Chem.*, 263:2409 (1988).
Renosto et al., *J. Biol. Chem.*, 259:2113 (1989).
Marcus et al., *Anal. Biochem.*, 107:296 (1980).
Suzuki et al., *Biochim. Biophys. Acta*, 50:169 (1961).
Robinson, *Biochem. J.*, 113:543 (1969).
Kimata et al., *Mol. Cell. Biochem.* 1:211(1973).
Silbert, *J. Biol. Chem.*, 239:1310 (1964).
Kim et al., *J. Biol. Chem.*, 252:8292 (1977).
Habuchi et al., *Biochim. Biophys. Acta*, 208:616 (1980).
Habuchi et al., *Biochim. Biophys. Acta*, 414:717 (1982).
Habuchi et al., *J. Biol. Chem.*, 246:7357 (1971).
Nakanishi et al., *J. Biol. Chem.*, 256:5443 (1981).
Sugumaran et al., *J. Biol. Chem.*, 261:12659 (1986).
Fisher et al., *Nature*, 357:655 (1992).
LeRouge et al., *Nature*, 344:781 (1990).
Faucher et al., *Mol. Plant–Microbe Interactions*, 2:291 (1989).
Faucher et al., *J. Bacteriol.*, 170:5489 (1988).
Atkinson et al., *Proc. Natl. Acad. Sci., USA*, 91:8418 (1994).
Schwedock et al., *Mol. Plant–Microbe Interactions*, 2:181 (1989).
Cervantes et al., *Mol. Microbiol.*, 3, 745 (1989.
Roche et al., *Cell*, 67:1131 (1991).
Seubert et al., *Arch. Biochem. Biophys.*, 115:679 (1983).
Renosto et al., *J. Biol. Chem.*, 264:9433 (1989).
Burnell et al., *Anal. Biochem.*, 68:281 (1975).
Ogura et al., *Molecular Pharmacol.*, 27:848 (1990).

*Primary Examiner*—John W. Rollins
*Assistant Examiner*—Francisco C. Prats
*Attorney, Agent, or Firm*—Welsh & Katz, Ltd.

[57] ABSTRACT

A process for the enzymatic synthase of sulfate esters is disclosed in which intermediate phosphorylated adenosine compounds are recycled to minimize enzyme inhibition. Exemplary enzymes include ATP sulfurylase, APS kinase and a sulfotransferase.

6 Claims, 4 Drawing Sheets

ONE-POT ENZYMATIC SULFATION PROCESS USING 3'-PHOSPHOADENOSINE-5'-PHOSPHOSULFATE AND RECYCLED PHOSPHORYLATED ADENOSINE INTERMEDIATES

DESCRIPTION

1. Technical Field

The present invention relates to the enzymatic synthesis of sulfate esters, and more particularly to a single vessel enzyme-catalyzed sulfation of an acceptor molecule by 3'-phosphoadenosine-5'-phosphosulfate in which intermediate phosphorylated adenosine compounds are recycled.

2. Background Art

Sulfated biomolecules play important roles in many biological processes [Varki, *Glycobiology*, 3:97 (1993)]. For example, the sulfated Lea tetra- and pentasaccharides [Yuen et al., *J. Biol. Chem.*, 269:1595 (1994)] are potent E-selectin inhibitors and sialyl Lewis x with a sulfate group at the 6-position of galactose is a ligand for L-selectin [Hemmerich et al., *Biochemistry*, 33:4830 (1994)]. These sulfated sugars play important roles in cell adhesion in response to inflammatory reactions [Varki, *Proc. Natl. Acad. Sci.*, 91:7390 (1994)]. Many glycosaminoglycans are also sulfated and are involved in numerous cellular functions [van Boeckel et al., *Angew. Chem. Int. Ed. Eng.*, 32:1671 (1993)]. In addition, the sulfation of hydroxysteroids provides hydrophilic forms for excretion [Ogura et al., *Biochem. Biophys. Res. Commun.*, 165:169 (1989)].

In the course of sulfation, inorganic sulfate is activated first, followed by a transfer of the sulfate group to the final acceptor [Bernstein et al., *J. Biol. Chem.*, 199:745 (1952)]. The two key enzymes involved in this activation process are ATP sulfurylase (EC 2.7.7.4) and adenosine-5'-phosphosulfate (APS) kinase (EC 2.7.1.25) [Robbins et al., *J. Biol. Chem.*, 233:686 (1958)]; their reactions are shown in Scheme 1, below, in which "A" is adenosine, "ROH" is the acceptor, and "PPi" is pyrophosphate, following usually used abbreviations.

Scheme 1

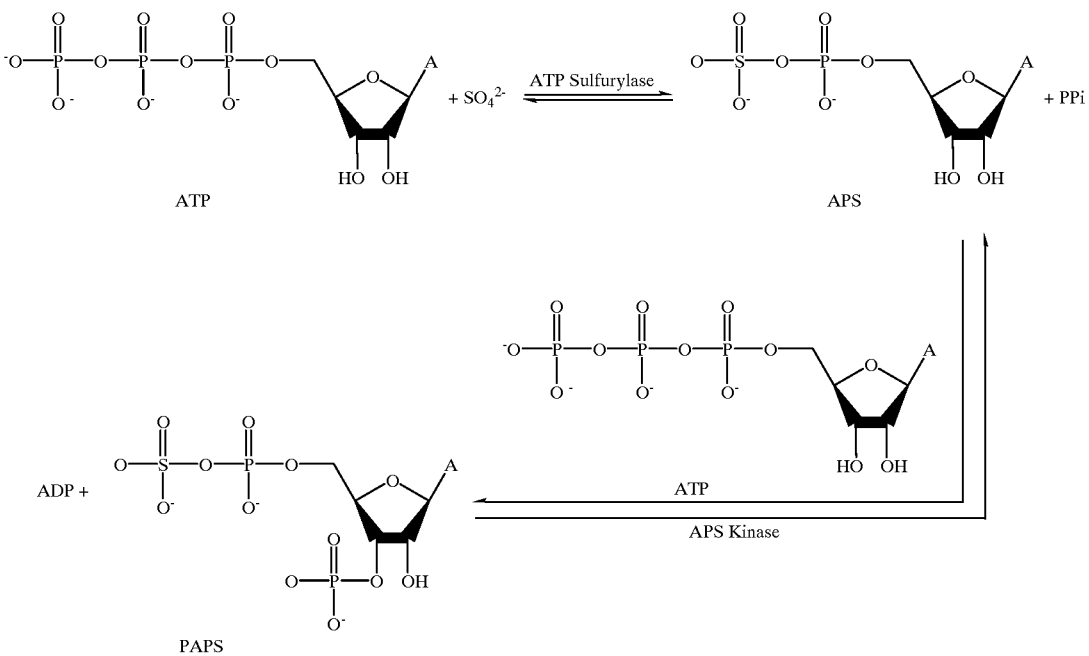

3'-Phosphoadenylsulfate, also known as 3'-phosphoadenosine-5'-phosphosulfate (PAPS), is the product generated in these two enzymatic reactions and is a substrate and cofactor for the enzymatic sulfation of oligosaccharides and steroids using sulfotransferases. Of the twenty-eight sulfotransferase enzymes [EC 2.8.2.1-28] listed in *Enzyme Nomenclature* 1992, E. C. Webb, ed., Academic Press, San Diego, Calif. 1992, pages 299–303, all but one enzyme utilize PAPS as the sulfate donor.

Several groups have reported the synthesis of PAPS [Baddiley et al., *J. Am. Chem. Soc.*, 1731 (1959); Cherniak et al., *J. Biol. Chem.*, 239:1986 (1964); Sekura, *Methods in Enzymology*, 77:413 (1981); Horwitz et al., *Biochem. Biophy, Acta.*, 480:376 (1977); Satishchandran et al., *J. Biol. Chem.*, 264:15012 (1989); Fernando et al., *Biosci. Biotech. Biochem.*, 57:1974 (1993); Mukai, *Acric. Biol. Chem.* 53:883 (1989)]. The procedures involve many steps and gave very low yields [Baddiley et al., *J. Am. Chem. Soc.*, 1731 (1959); Cherniak et al., *J. Biol. Chem.*, 239:1986 (1964); Sekura, *Methods in Enzymoloqy*, 77:413 (1981); Horwitz et al., *Biochem. Biophy, Acta.*, 480:376 (1977)]. The enzymatic preparation of PAPS on nmol to μmol scales using isolated enzymes was described previously [Satishchandran et al., *J. Biol. Chem.*, 264:15012 (1989); Fernando et al., *Biosci. Biotech. Biochem.*, 57:1974 (1993); Mukai, *Agric. Biol. Chem.* 53:883 (1989)]; however, it was not clear if the process was feasible for larger scale synthesis.

Recently, the genes coding for ATP sulfurylase and APS kinase in *E. coli* have been identified [Leyh et al., *J. Biol. Chem.*, 263:2409 (1988)]. These genes are located in the cluster of cys CDHIJ of *E. coli*. ATP sulfurylase contains two different subunits corresponding to two genes, cys D and cys N. APS kinase contains one subunit corresponding to the cys C gene.

ATP is a substrate for ATP sulfurase and is a cofactor/substrate for APS kinase. ADP, a product of the APS kinase-catalyzed reaction, is an inhibitor of APS kinase. [Satishchandran et al., *J. Biol. Chem.*, 264:15012 (1989)]. APS is both a substrate/cofactor and inhibitor in the APS kinase reaction and a product and inhibitor in the APS sulfurase reaction [Renosto et al., *J. Biol. Chem.*, 259:2113 (1989)]. In addition, the cofactor/product of the sulfotransferase reaction, 3'-phosphoadenosine 5'-phosphate (PAP; also known as adenosine 3',5'-bisphosphate), inhibits the sulfotransferase [Marcus et al., *Anal. Biochem.*, 107:296 (1980)].

In view of the inhibitions caused by the several products and substrates for the above reactions, one way to produce relatively large amounts of PAPS would be to use very low levels of those substrates and products in a large volume, or the use of a high concentration of enzyme. Neither approach appears promising where use of PAPS is desired in a large scale synthesis.

The disclosure that follows illustrates a process in which intermediate substrate and product phosphorylated adenosine compound concentrations are minimized to minimize inhibitory reactions, while not necessitating a high concentration of an enzyme or large volume to obtain a high yield of a sulfated product.

BRIEF SUMMARY OF THE INVENTION

A process for using 3'-phosphoadenine-5'-phosphosulfate (PAPS) in an enzyme-catalyzed sulfation of an acceptor is contemplated. That process recycles phosphorylated adenosine intermediates and comprises the steps of:
(a) admixing the following ingredients in an aqueous medium containing magnesium and potassium ions within a single vessel to form an aqueous reaction medium
   (i) 3'-nucleotidase or 3'(2'),5'-bisphosphate nucleotidase;
   (ii) ATP sulfurylase;
   (iii) APS kinase;
   (iv) pyrophosphorylase;
   (v) a sulfotransferase;
   (vi) at least one phosphorylated adenine-containing compound selected from the group consisting of ATP, ADP, AMP, PAPA and PAP;
   (vii) sulfate ion;
   (viii) an ATP-regenerating system comprising a phosphate donor and a phosphorylating enzyme; and
   (ix) a sulfate acceptor for the sulfotransferase.
The concentration of the sulfate ion is greater than the concentration of the phosphorylated adenine-containing compound in an above process, and the activity of the 3'-nucleotidase or 3'(3'),5'-bisphosphate nucleotidase is less than that of the enzymes of (ii)–(v).

The aqueous reaction medium is maintained at a pH value of about 5 to about 10 at a temperature of about zero degrees C to about 40° C. for a time period sufficient for the acceptor to be sulfated. The sulfated acceptor is thereafter preferably recovered.

A process of Scheme 3, hereinafter, for using APS to prepare PAPS with recycling of ATP and ADP thus comprises the steps of:
(a) admixing the following ingredients in an aqueous medium containing magnesium and potassium ions within a single vessel to form an aqueous reaction medium
   (i) ATP sulfurylase;
   (ii) APS kinase;
   (iii) pyrophosphatase;
   (iv) at least one phosphorylated adenine-containing compound selected from the group consisting of ADP, ATP and APS;
   (v) sulfate ion; and
   (vi) an ATP-regenerating system comprising a phosphate donor and a phosphorylating enzyme, wherein the phosphorylated adenine-containing compound is present at a concentration that is less than that of the sulfate ion.
The aqueous reaction medium so formed is (b) maintained at a pH value of about 5 to about 10 at a temperature of about zero degrees C to about 40° C. for a time period sufficient for PAPS to form.

BRIEF DESCRIPTION OF THE DRAWINGS

In the drawings forming a portion of this disclosure.

DETAILED DESCRIPTION OF THE INVENTION

Figure 1:
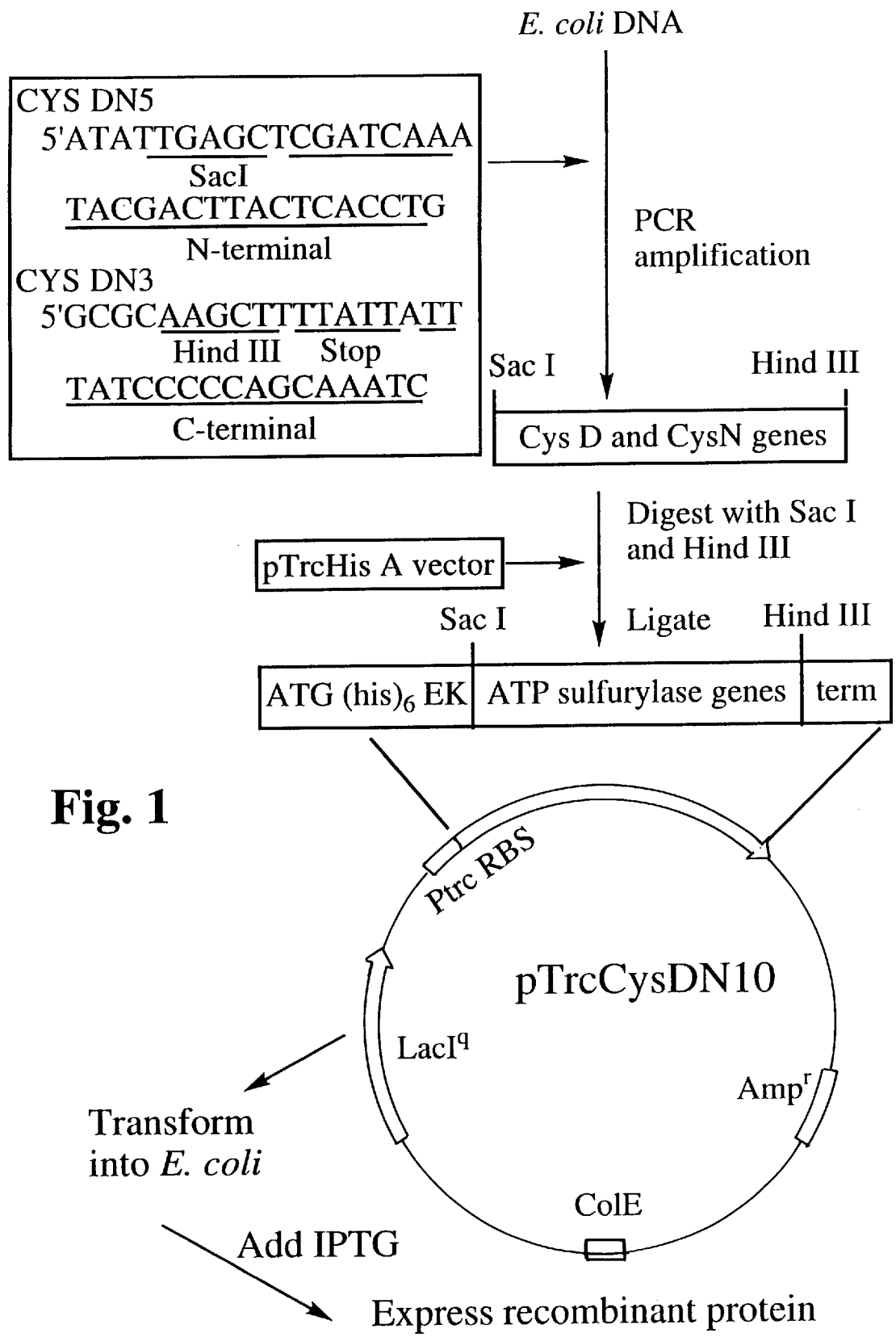
FIG. 1 is a schematic representation of the steps utilized in preparing recombinant ATP sulfurase beginning with *E. coli* DNA. That DNA is subjected to PCR amplification using primers CYS DN5 and CYS DN3 (SEQ ID NOs: 1 and 2, respectively) that contain Sac I and Hind III restriction sites at their 5'- and 3'-termini. Bases present in the native sequence are underlined. That amplification is followed by digestion with those enzymes and ligation of the Sac I-Hind III fragment into vector pTrcHisA to form vector pTrcCys-DNIO. That latter vector, once transformed into *E. coli* and induced with isopropylthio-β-D-galactoside (IPTG), expresses the recombinant enzyme.

ATP sulfurase, APS kinase and sulfotransferase are membrane-bound enzymes found in the Golgi apparatus of cells where the enzymes are typically involved in sulfating saccharide units of proteoglycan molecules. In a living organism, the synthesis of PAPS as shown in Scheme 1 suffices for the cell's needs, and it may not matter to the organism if PAP formed from using PAPS to sulfate a molecule inhibits a later reaction. Indeed, the degradation of PAPS observed in vitro may also be of little consequence in vivo because effects of cellular synthesis location that cause the formed PAPS to be used about as fast as it is produced.

In vitro synthetic systems do not have the benefit of billions of years of evolution. Such in vitro systems are usually designed to maximize yield, and to do so, take concentration-dependent inhibitions into account as well as the instability of the sulfate donor (PAPS) and the fact that PAP is an inhibitor of enzymes involved in the sulfation process for which it is not a substrate, a cofactor or a product. One embodiment of the present invention provides a process through which high yields of sulfated product are obtained, in which concentration-dependent inhibitions are minimized, and in which PAP-mediated inhibition is minimized.

This process takes place in a single vessel ("one-pot") and is a cyclic process in which phosphorylated adenosine-containing moieties including AMP, ADP, ATP, APS, PAPS and PAP are recycled while more and more sulfate product is prepared. A schematic representation of this process is shown in Scheme 2, below wherein "PEP" is phosphoenolpyruvate" and "Pyr" is pyruvate.

Scheme 2

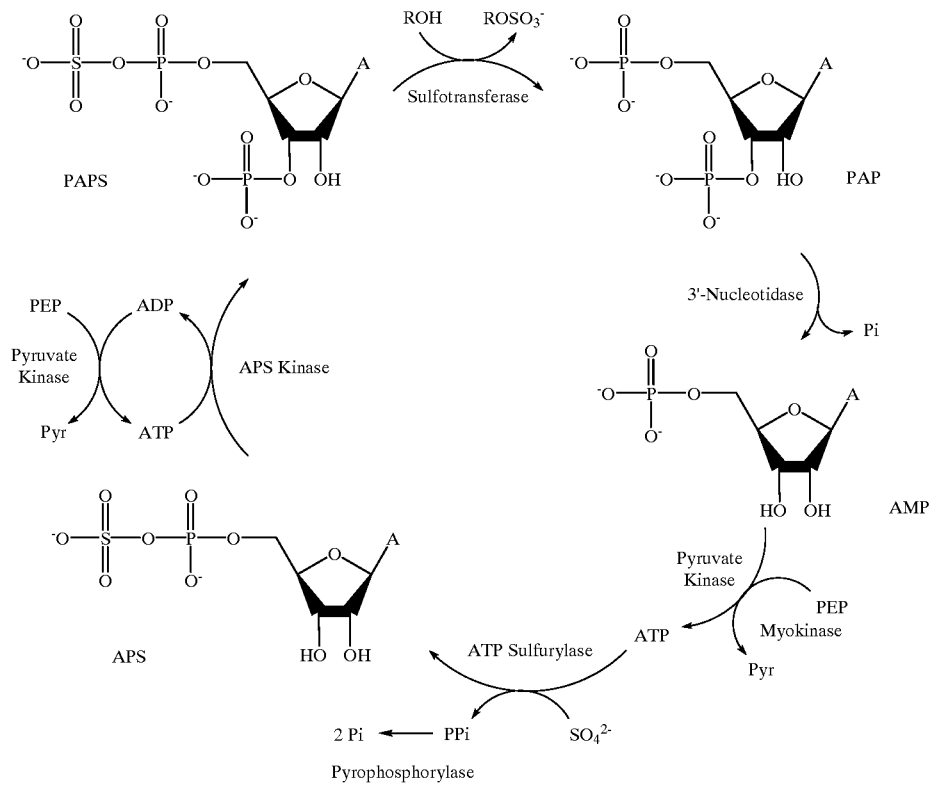

One of the key features of the above process is its preferred use of 3'-nucleotidase (EC 3.1.3.6) to hydrolyze the 3'-phosphate of PAP to form adenosine monophosphate (AMP). 3'(2'),5'-Bisphosphate nucleotidase (EC 3.1.3.7) can also be used in that step. These AMP-forming enzymes are not normally found in conjunction with Golgi membranes. In addition, 3'-nucleotidase usually hydrolyzes adenosine 3'-phosphate, and the finding that that enzyme could convert PAP to AMP is thought to be new. This formation of AMP removes PAP from the system to minimize the product inhibitory effect of that molecule on the sulfotransferase. This reaction also forms a new intermediate phosphorylated adenosine-containing molecule that can be formed into ADP and ATP via pyruvate kinase (PK; EC 2.7.1.40) and adenylate kinase (myokinase; EC 2.7.4.3) and reused in the synthesis.

Once the AMP is regenerated into ATP, that molecule reacts with sulfate ion in the presence of ATP sulfurase to form APS and inorganic pyrophosphate (PPi) Hydrolysis of pyrophosphate into two moles of inorganic phosphate (Pi) by an enzyme such as pyrophosphorylase (EC 3.6.1.1) removes the pyrophosphate. Another mole of ATP is utilized to react with APS in the presence of APS kinase to form PAPS, the substrate for the sulfotransferase and sulfate acceptor.

The ATP sulfurylase-catalyzed sulfation reaction actually favors the reverse of the reaction shown. However, the forward reaction is driven as shown by the degradation of pyrophosphate into inorganic phosphate, another key feature of this process.

The above one-pot, cyclic reaction is also driven in the direction shown by phosphorylation reactions before and after APS formation that involve PEP and pyruvate kinase, as shown in Scheme 2. It should be understood, however, that other phosphate donors and phosphorylating enzymes can be used. For example, ADP can be converted to ATP by use of acetylphosphate as phosphate donor and acetate kinase (EC 2.7.2.1) as the phosphorylating enzyme.

The PEP-pyruvate kinase and myokinase or another donor-enzyme system can be more generally referred to as an ATP-regenerating system comprising a phosphate donor and phosphorylating enzyme that can form ATP using the phosphate donor. The myokinase, pyruvate kinase-PEP/Pyr system is preferred.

Each of the enzymes used in a contemplated process is known in the art and can be obtained using literature procedures, as was the case for the chondroitin 6-sulfotransferase used herein. Exemplary literature citations for these enzymes can be found in *Enzyme Nomenclature* 1992, E. C. Webb, ed., Academic Press, San Diego, Calif. (1992), and include those in the table below.

TABLE

| E.C. No. | Name |
| --- | --- |
| 2.8.2.1 | Aryl sulfotransferase |
| 2.8.2.2 | Alcohol sulfotransferase |
| 2.8.2.3 | Amine sulfotransferase |
| 2.8.2.4 | Estrone sulfotransferase |
| 2.8.2.5 | Chondroitin 4-sulfotransferase |
| 2.8.2.6 | Choline sulfotransferase |
| 2.8.2.7 | UDP-N-acetylgalactosamine-4-sulfate sulfotransferase |
| 2.8.2.8 | Desulfoheparin sulfotransferase |
| 2.8.2.9 | Tyrosine-ester sulfotransferase |
| 2.8.2.10 | Renilla-luciferin sulfotransferase |
| 2.8.2.11 | Galactosylceramide sulfotransferase |
| 2.8.2.12 | Heparitin sulfotransferase |
| 2.8.2.13 | Psycosine sulfotransferase |
| 2.8.2.14 | Bile-salt sulfotransferase |
| 2.8.2.15 | Steroid sulfotransferase |
| 2.8.2.16 | Thiol sulfotransferase |
| 2.8.2.17 | Chondroitin 6-sulfotransferase |
| 2.8.2.18 | Cortisol sulfotransferase |
| 2.8.2.19 | Triglycosylalkylacylglycerol sulfotransferase |
| 2.8.2.20 | Protein-tyrosine sulfotransferase |
| 2.8.2.21 | Keratan sulfotransferase |
| 2.8.2.23 | Heparin-glucosamine 3-O-sulfotransferase |
| 2.8.2.24 | Desulfoglucosinolate sulfotransferase |
| 2.8.2.25 | Flavonol 3-sulfotransferase |

TABLE-continued

| E.C. No. | Name |
| --- | --- |
| 2.8.2.26 | Quercetin-3-sulfate 3'-sulfotransferase |
| 2.8.2.27 | Quercetin-3-sulfate 4'-sulfotransferase |
| 2.8.2.28 | Quercetin-3,3'-bissulfate 7-sulfotransferase |

Other enzymes such as pyruvate kinase and acetate kinase are available commercially as from Sigma Chemical Co., St. Louis, Mo. or Boeringer Mannheim, Indianapolis, Ind. Four of the enzymes used herein, ATP sulfurase, APS kinase, hydroxysteroid sulfotransferase (HSSTase) and NodH (NodHST) sulfotransferase were cloned in *E. coli*, after amplification by PCR using the primers of SEQ ID NOs:1–8, as is discussed hereinafter.

Because of the cycling of phosphorylated adenosine-containing compounds utilized in a contemplated process, only one of AMP, ADP, ATP, APS, PAPS and PAP need be present initially with the enzymes, sulfate, ATP-regenerating system and sulfate acceptor. It is preferred, however, that ATP be present in the original reaction mixture.

It is also preferred that an adenosine phosphate other than PAP, APS and ADP be initially absent from the reaction medium because-of their inhibitory activities on the enzymes.

Regardless of which of those adenosine phosphate-containing compounds is initially present, each of those compounds is formed, used and-formed again cyclically as the reaction proceeds to form the sulfated product. This cyclic reuse of phosphorylated adenosine compounds is another salient feature of a contemplated process.

A contemplated process is carried out in an aqueous medium at a pH value of about 5 to about 10, and preferably at about pH 6.5 to about 8.5 in buffer. The temperature at which the process is carried out can be from about zero degrees C to about 40° C., and preferably at about 20° C. to about 35° C. Reactions are carried out at atmospheric pressure. Water-miscible organic solvents such as DMSO or acetone can be present at up to about 5 volume percent of the aqueous reaction medium. The aqueous medium also contains about 5 to about 30 mM KCl, and about 1 to about 10 mM $MgCl_2$ or other source of magnesium ions.

Sulfate ion is also present in the reaction medium. The concentration of sulfate is preferably in excess over ATP (viewed as all of the adenosine phosphates) by ratio of 2:1 to about 10:1. Equal amounts of sulfate ion and ATP can also be used.

The reaction is maintained under the above conditions for a period of time sufficient to form a desired sulfated product. Typical reaction times range from about one hour to about five days.

A contemplated process thus comprises the steps of:
(a) admixing the following ingredients in an aqueous medium containing magnesium and potassium ions within a single vessel to form an aqueous reaction medium
  (i) 3'-nucleotidase or 3'(2'),5'-bisphosphate nucleotidase;
  (ii) ATP sulfurylase;
  (iii) APS kinase;
  (iv) pyrophosphorylase;
  (v) a sulfotransferase;

(vi) at least one phosphorylated adenine-containing compound selected from the group consisting of ATP, ADP, AMP, PAPA and PAP;
(vii) sulfate ion;
(viii) an ATP-regenerating system comprising a phosphate donor and a phosphorylating enzyme; and
(ix) a sulfate acceptor for the sulfotransferase.

The concentration of the sulfate ion is greater than the concentration of the phosphorylated adenine-containing compound in an above process, and the activity of the 3'-nucleotidase or 3'(2'),5'-bisphosphate nucleotidase is less than that of the enzymes of (ii)–(v). The aqueous reaction medium so formed is (b) maintained as discussed before.

Once formed, the sulfated product is preferably recovered, although the product can be left place for the carrying out of a further reaction(s) on the product, such as one or more further glycosyl transfer reactions. Products are typically recovered by well known chromatographic techniques, some of which are discussed hereinafter.

Another aspect of the present invention is shown in Scheme 3, that is shown below as were Schemes 1 and 2, and wherein "Pi" is inorganic phosphate. Scheme 3 illustrates a cyclic process that results in a buildup of PAPS via recycling of the phosphorylated adenosine compounds ATP and ADP.

Scheme 3

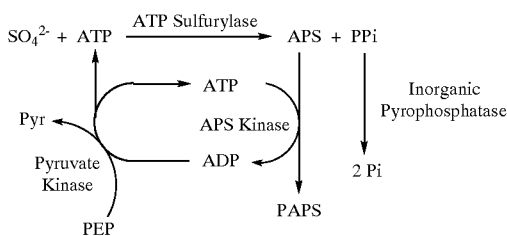

The reaction scheme illustrated in Scheme 3 provides an apt synthetic procedure for preparing PAPS, were that compound a stable, desired end product. Unfortunately, PAPS is not itself very long lived in aqueous solution, so the pathway shown in Scheme 3 that uses two moles of ATP for each mole of PAPS formed is not as useful as might be desired in a large scale sulfation.

A process of Scheme 3, above, for using APS to prepare PAPS with recycling of ATP and ADP thus comprises the steps of:
(a) admixing the following ingredients in an aqueous medium containing magnesium and potassium ions within a single vessel to form an aqueous reaction medium
    (i) ATP sulfurylase;
    (ii) APS kinase;
    (iii) pyrophosphatase;
    (iv) at least one phosphorylated adenine-containing compound selected from the group consisting of ADP, ATP and APS;
    (v) sulfate ion; and
    (vi) an ATP-regenerating system comprising a phosphate donor and a phosphorylating enzyme, wherein the phosphorylated adenine-containing compound is present at a concentration that is less than that of the sulfate ion.

The aqueous reaction medium so formed is (b) maintained at a pH value of about 5 to about 10 at a temperature of about zero degrees C to about 40° C. for a time period sufficient for PAPS to form. The enzymes, reagents and process conditions are as discussed before. Recovery is again preferred and is discussed before, although in situ, non-cyclic use of PAPS can also be made using a before-described sulfotransferase enzyme.

As was the case with the previously described process, one can start the process with any of the three named phosphorylated adenine-containing compounds. It is preferred that at least ATP be present initially. As is also seen from Scheme 3, two moles of ATP are required to form one mole of PAPS, with one of those two moles of ATP being sulfated to form APS, whereas the second mole phosphorylates APS to form PAPS and ADP. The ADP so formed is then formed into ATP again that can form APS and be phosphorylate to PAPS. Thus, in theory, one-half of the ATP is consumed on each cycle of the reaction.

Results

Amplification of cys DN and cys C genes

Figure 2:
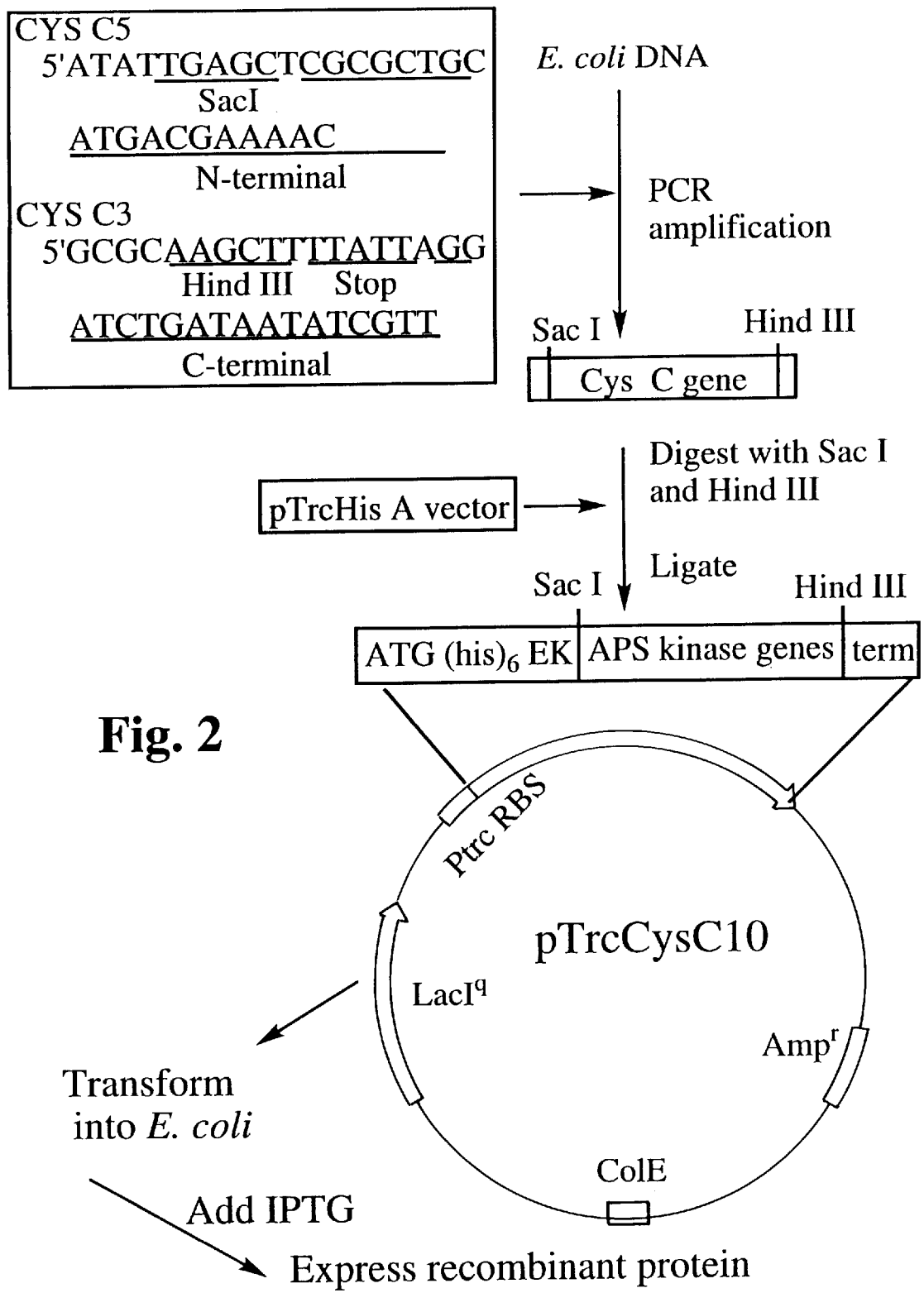
FIG. 2 is a schematic representation similar to that of FIG. 1 showing the steps utilized in preparing recombinant APS kinase. Here, primers CYS C5 and CYC C3 (SEQ ID NOs: 3 and 4, respectively) that also contain Sac I and Hind III restriction sites were used, with the remaining steps being similar to those in FIG. 1.

Two primers cys DN5 and cys DN3 were designed to specifically complement with the C-terminal and N-terminal gene sequences of ATP sulfurylase (cys D and cys N genes). Leyh et al., J. Biol. Chem., 268:2409 (1988). The other two primers, cys C5 and cys C3 were designed to specifically complement with the N- and C-terminal sequences of APS kinase (cys C gene). Leyh et al., J. Biol. Chem., 268:2409 (1988). The sequences of the primers are shown in FIGS. 1 and 2 (SEQ ID NOs: 1–4).

The primers cys DN5 and cys C5 contained a Sac I restriction site and the N-terminal six amino acid sequences of the genes. The primer cys DN3 and cys C3 contained a Hind III restriction site, stop codons, and the C-terminal six amino acid sequences of the genes. After PCR amplification, only one band was observed with molecular weight about 2.3 kb that was consistent with the reported gene size of ATP sulfurylase, and another band of 800 bp correlated well with the APS kinase gene size. Leyh et al., J. Biol. Chem., 268:2409 (1988).

Construction of the Expression Vector and Screening for Positive Clones

After ligation of the digested vector and inserts, the DNA was transformed into E. coli XL1-Blue MRF' strain and plated on the LB-ampicillin plates. The colonies were randomly selected from the plates and subjected to PCR amplification. Out of 20 colonies selected for ATP sulfurylase, 12 colonies showed that the PCR amplification product contained a 2.3 kb DNA band.

One clone that gave the highest band intensity was selected for further confirmation of the insert. That clone was assigned as strain E. coli cys DN-10, and the plasmid was assigned as pTrccysDN-10. For APS kinase, 43-colonies were randomly selected from the plates. After cell lysis, the lysates were used for PCR amplification. One clone identified as E. coli cys C-10 was selected, and its plasmid was designated pTrccysC-10.

Expression of Cloned ATP Sulfurylase and APS Kinase

The cloned E. coli cys DN-10 and cys C-10 were grown on LB medium [Sambrook et al., Molecular Cloning, 2nd ed., Cold Spring Harbor Laboratory, New York (1989)] containing 150 μg/mL ampicillin and induced with 0.5 mM IPTG as described hereinafter in the Materials and Methods Section. The expression level of the enzyme was followed with time and examined with SDS acrylamide gel. When the cells were growing at 37° C., the recombinant proteins were formed as inclusion bodies. Lowering the growing temperature to 25° C. provided the proteins expressed as the soluble form after two hours of IPTG addition. The proteins remained soluble after 20 hours of induction.

The activity of the expressed ATP sulfurylase was determined to be about 430 U/L, and that of APS kinase was about 560 U/L. After the ammonium sulfate fractionation, 80 percent of the enzyme activities in the cell extract were recovered and used for further purification.

Preparation and Partial Purification of ATP Sulfurylase and APS Kinase

The use of crude extract as the source of the two enzymes in the synthesis of PAPS failed because of the presence of contaminant proteins, mainly the existing hydrolases, which were involved in the degradation of adenosine 5'-phosphosulfate (APS) and PAPS. Renosto et al., *J. Biol. Chem.*, 259:2113 (1984). The problem was overcome using partially purified enzymes prepared via ammonium sulfate precipitation and ion exchange chromatography on DEAE Sepharose.

Synthesis of PAPS Using ATP Sulfurylase and APS Kinase

To apply these two enzymes to the synthesis of PAPS, the PAPS yield was optimized by controlling the reaction time, as PAPS is highly unstable. According to the information provided from the catalog of Sigma Co. 1993, 46. The maximum yield was about 60 percent based on the consumption of ATP. [The yield was determined on FPLC using a Mono-Q ion exchange column and a UV detector (254 nm), see Materials and Methods]. It is noted that two equivalents of ATP are required for each equivalent of PAPS produced.

As indicated in Table 1 below, when the concentration of $SO_4^{2-}$ was higher than that of ATP, a better reaction yield was obtained (entries 1 to 4). Furthermore, increasing the concentration of $SO_4^{2-}$ relative to ATP also led to a higher yield of the enzymatic reaction (entries 1, 2, 7, 8, 9). This result is consistent with the fact that the equilibrium of the ATP sulfurylase reaction lies far to the left. Robbins et al., *J. Biol. Chem.*, 233:686 (1958); Satishchandran et al., *J. Biol. Chem.*, 264:15012 (1989); Seubert et al., *Arch. Biochem. Biophys.*, 225:679 (1983); Renosto et al., *J. Biol. Chem.*, 264:9433 (1989). On the other hand, the concentration of $Mg^{2+}$ did not effect the reaction yield (entries 1, 5, 6).

TABLE 1

Enzymatic Synthesis of PAPS
Under Different Reaction Conditions

| Entry | ATP (mM) | Na$_2$SO$_4$ (mM) | MgCl$_2$ (mM) | Yield (%) |
|---|---|---|---|---|
| 1 | 5 | 5 | 5 | 30.5 |
| 2 | 5 | 10 | 5 | 34.7 |
| 3 | 10 | 10 | 5 | 22.3 |
| 4 | 10 | 5 | 5 | 5.3 |
| 5 | 5 | 5 | 10 | 31.7 |
| 6 | 5 | 5 | 20 | 30.2 |
| 7 | 5 | 20 | 5 | 38.8 |
| 8 | 5 | 30 | 5 | 43.2 |
| 9 | 5 | 40 | 5 | 45.6 |

*The enzymatic reaction proceeded in 0.5 mL of Tris-HCl (50 mM, pH 8.0), containing 20 mM KCl, 1 U of ATP sulfurylase, 3.5 U of APS kinase, 2 U of inorganic pyrophosphatase, ATP, Na$_2$SO$_4$, MgCl$_2$.

In order to maximize the yield and to reduce the accumulation of ADP that can cause product inhibition, [Satishchandran et al., *J. Biol. Chem.*, 264:15012 (1989)] regeneration of ATP from ADP by using pyruvate kinase (EC 2.7.1.40) and phospho(enol)pyruvate (PEP) was carried out as shown in Scheme 3, before.

As shown in Table 2, below, an 82.3 percent yield of PAPS was accomplished using 2 mM of ATP in such a regeneration system. The reaction yield remained unchanged when scaled up to 100 mg (see Materials and Methods).

TABLE 2

ATP Regeneration and Concentration
Effects on the Enzymatic Synthesis of PAPS

| Entry | ATP (mM) | PEP (mM) | Yield (%) |
|---|---|---|---|
| 1 | 5 | —[a] | 45.6 |
| 2 | 5 | 5[b] | 63.2 |
| 3 | 2 | —[a] | 47.1 |
| 4 | 2 | 2[b] | 82.3 |

[a]: The enzymatic reaction proceeded in 0.5 mL of Tris-HCl (50 mM, pH 8.0), containing 20 mM KCl, 40 mM Na$_2$SO$_4$, 5 mM MgCl$_2$, 1 U of ATP sulfurylase, 3.5 U of APS kinase, 2 U of inorganic pyrophosphatase, ATP.
[b]: The reaction condition is the same as a, except 20 U of pyruvate kinase, PEP were included.

The lower yield at higher concentrations of ATP may be related to the problem of product and substrate inhibition of ATP sulfurylase and APS kinase [Renosto et al., *J. Biol. Chem.*, 259:2113 (1984)] in the APS kinase reaction, the $K_i$ value of APS is 23 μM, [Renosto et al., *J. Biol. Chem.*, 259:2113 (1984)] and in the ATP sulfurylase reaction, APS shows a strong product inhibition ($K_i$<0.25 μM). Seubert et al., *Arch. Biochem. Biophys.*, 225:679 (1983).

PAPS prepared in this study was then used in the enzymatic sulfation of a hydroxysteroid and chondroitin. In addition, regeneration of PAPS from 3'-phosphoadenosine-5'-phosphate (PAP) was demonstrated in the enzymatic sulfation of the hydroxysteroid as is shown schematically in Scheme 5 hereinafter in the Materials and Methods Section.

Materials and Methods

Enzymatic Synthesis and Generation of PAPS

Reagents

The vector pTrcHis was obtained from Invitrogen Co. (San Diego, Calif.). The vector contains the Trc promoter to permit a high expression of protein. The Trc promoter has the −35 region of the Trp promoter fused with the −10 region of the lac promoter. This promoter is repressed by the lac repressor, provided by a copy of the lacIq gene encoded by the vector. All the other chemicals were purchased from commercial sources as molecular biology grade reagents.

Microorganism

*E. coli* K12 (ATCC 10798) was obtained from American Type Culture Collection. The host strains *E. coli* XL1-Blue and XL1-Blue MRF' were purchased from Stratagene Co. (San Diego, Calif.). The microorganisms were maintained on LB (Luria-Bertani) medium. When host strains harbored plasmid vectors, LB medium containing 100 μg/mL of ampicillin was used. Stock cultures were kept as cell suspensions at −70° C. in 20 percent glycerol solution.

DNA manipulation The DNA of *E. coli* K12 was extracted according to the method described in Sambrook et al., *Molecular Cloning*, 2nd ed., Cold Spring Harbor Laboratory, New York, 1989. Vector pTrcHis A was transformed into *E. coli* XL1-Blue strain and prepared as described also by Sambrook et al., *Molecular Cloning*, 2nd ed., Cold Spring Harbor Laboratory, New York, 1989. Primers were custom synthesized and purified by acrylamide gel electrophoresis.

Amplification of the Cys DN and Cys C Genes

PCR amplifications were performed in a 100 μL reaction mixture containing 1 μL (1.5 μg) of *E. coli* K12 DNA, 300 nmoles of primers cys DN5 and cys DN3 (shown in FIG. 1 and SEQ ID NOs:1 and 2, respectively; ATP sulfurylase) or cys C5 and cys C3 (shown in FIG. 2 and SEQ ID NOs:3 and 4, respectively; APS kinase), 200 μM of different dNTPs, 50 mM KCl, 10 mM Tris-HCl (pH 8.3), 2 mM MgCl$_2$, 0.01 percent gelatin, 0.1 percent Triton X-100, and 2 units of *Thermus aquaticus* DNA polymerase. The reaction was overlayered with mineral oil and subjected to 35 cycles of amplifications. The cycle conditions were set as follows: denaturation, 94° C. for one minutes, 55° C. for two minutes; and elongation, 72° C. for 1.5 minutes.

Construction of ATP Sulfurylase and APS Kinase Expression Vectors

The DNA insert obtained from PCR amplification was purified on 0.7 percent agarose gel. The DNA band corresponding to this insert was separated from the agarose gel and purified with Gene Clean kit (Bio 101, San Diego, Calif.). The DNA was dissolved in an appropriate restriction enzyme buffer (H buffer) supplied by Boehringer Mannheim Biochemical Co. (Indianapolis, Ind.) and digested with Sac I and Hind III each with 35 U/μg DNA at 37° C. for two hours. The digested DNA was then recovered by phenol/chloroform extraction and ethanol precipitation (70 percent of final ethanol concentration containing 10 percent of 3N sodium acetate, pH 5.2) and purified by agarose (0.7 percent) gel electrophoresis. The DNA band was isolated from the agarose gel and extracted with QIAEX gel extraction kit (Qiagen Co., Chatworth, Calif.) and eluted with TE buffer (10 mM Tris.HCl and 1 mM EDTA, pH 7.5). This DNA was used as insert. The vector pTrcHis A was also digested with 5 U/μg DNA of Sac I and Hind III and recovered with ethanol precipitation after extraction with phenol/chloroform. The digested vector was further purified in agarose gel as described above. The insert was then ligated with the vector by T4 DNA ligase. Sambrook et al., *Molecular Cloning*, 2d ed., Cold Spring Harbor Laboratory, New York, 1989. The ligated DNA was then transformed into *E. coli* XL1-Blue MRF' strain and plated on LB agar plates containing 250 μg/mL ampicillin.

Screening for Positive Clones and Expression of the Targeted Protein

The PCR method was used for screening for positive clones. Because the host *E. coli* XL1-Blue also contains a similar gene, there may have some background amplification for non-recombinants. However, the positive clones showed a very intense color band on agarose gel (0.7 percent) due to the high copy number of the target gene presented in the cells. Thirty colonies were randomly selected from plates and lysed with 50 μL of cell lysing buffer (20 mM Tris-HCl containing 1 percent Triton X-100 and 2 mM EDTA, pH 8.5) and heated with boiling water for five minutes. The solution was used directly as a DNA template source for PCR amplification after cooling. The procedure for the PCR amplification was the same as described above except 3 μL of the cell lysing solution were used to replace *E. coli* DNA. The colonies that gave intense PCR amplification were further grown on LB medium containing 150 μg/mL ampicillin and then the plasmids were extracted. The isolated plasmids were further digested with SacI and Hind III restriction enzymes and analyzed with agarose gel to confirm the target gene insert. The positive clones were selected and used for protein expression.

Growing Transformed *E. coli* Strain

To express the desired protein, the positive clone was grown on 100 mL of LB medium containing 250 μg/mL ampicillin at 37° C. with shaking (300 rpm). After the cell growth reached to mid-logarithmic phase ($OD_{600}$ 0.3–0.4), this culture was transferred to a fresh 4-L LB medium containing 250 μg/mL ampicillin, cultured at 37° C. until $OD_{600}$ reached 0.4, and then induced with 0.5 mM IPTG at 25° C. for 20 hours with shaking. The expression level of the targeted protein was analyzed by SDS-PAGE using Pharm System (Pharmacia Co.) with a 10–15 percent gradient of polyacrylamide.

Preparation of Partially Purified Enzyme Solution for Organic Synthesis

The culture broth was centrifuged (9,000×g, 20 minutes, 4° C.), and then suspended in 50 mL of Tris-HCl buffer (50 mM, pH 7.6). The cells were disrupted in a French pressure cell at 16,000 lb/in$^2$ and centrifuged at 18,000×g for 50 minutes. The supernatant was collected and the protein was fractionated with ammonium sulfate.

For APS kinase, 40–75 percent fraction of the ammonium sulfate precipitation was collected. In the case of ATP sulfurylase, 45 percent fraction of the ammonium sulfate precipitation was collected. Each protein was resuspended in Tris-HCl buffer (50 mM, pH 7.6) respectively. After dialysis against 4 L of the same buffer overnight (about 18 hours) at 4° C., the proteins were loaded on a column (40 cm×3 cm) packed with DEAE Sepharose 6B-CL, and eluted with a linear gradient of from 0 to 1.0M KCl (pH 7.6, total volume 0.5 L). The active fractions were pooled and used for organic synthesis without further purification.

Synthesis of PAPS using ATP Sulfurylase and APS Kinase

The quantitative determination of PAPS was carried out using an FPLC system (Pharmacia Co.). Varied concentrations of PAPS (purchased from Sigma co.) were prepared (e.g. 5 mM, 2.5 mM, 1.25 mM, 0.5 mM, 0.25 mm) and then applied onto a 0.5×5 cm of Mono-Q anion exchange column, with a UV monitor (254 nm). Satishchandran et al., *J. Biol. Chem.*, 164:15012 (1989). After loading, the column was first washed with 4 mL of water, then with a 55 mL gradient (from 50 mM to 1.0M $NH_4HCO_3$), and finally with 5 mL of 1.0 mM $NH_4HCO_3$. A linear relationship was established between the concentration of PAPS and the intensity of the signal detected by the UV monitor.

Tris-HCl buffer (100 mL; 50 mM, pH 8.0) containing 20 mM KCl, 40 mM $Na_2SO_4$, 5 mM $MgCl_2$, 2 mM ATP, 2 mM PEP, 20 U of ATP sulfurylase, 560 U of APS kinase, 400 U of inorganic pyrophosphatase, and 2000 U of pyruvate kinase was incubated at room temperature under N2. After 8 hours, the reaction solution was filtered to remove proteins and insoluble precipitates by using 10,000 NMWL regenerated cellulose membrane (Millipore Co., Bedford, Mass.).

The filtrate was chromatographed using a Mono-Q column as described above to give PAPS in 80.5 percent yield. The desired fractions were collected and the existing $NH_4HCO_3$ salt was then removed by Dowex 50W-X8 (H+). Fernando et al., *Biosci. Biotech. Biochem.*, 57:1974 (1993). The resin was repeatedly added until no more gas bubbles were emitted. To prevent PAPS from acid decomposition, it is important to keep the pH of the solution above 7.0. The resulting neutral solution was then lyophilized to give the product as white powder (76.8 mg, 72.7 percent overall yield). The TLC, FPLC, and 1H NMR data were identical to an authentic sample from Sigma Co.

Activity Assay

For APS kinase, the activity of the forward reaction (APS consumption) was measured using a modified pyruvate kinase-lactate dehydrogenase coupled assay of Burnell and Whatley. Burnell et al., *Anal. Biochem.*, 68:281 (1975). Thus, to 1 mL of Tris-HCl buffer (50 mM, pH 8.0) containing 5 mM Mg-ATP, 1 mM APS, 5 mM $MgCl_2$, 5 mM $Na_2SO_4$, 20 mM KCl, 0.3 mM NADH and 0.4 mM PEP, were added 50 U of pyruvate kinase, 50 U of lactate dehydrogenase, and 30 μL of APS kinase. The reaction was started by adding APS after the absorbance of NADH became constant. The decrease in NADH absorption at 340 nm was measured to determine the activity of APS kinase.

The reverse reaction was employed to assay ATP sulfurylase activity. Thus, to 1 mL of Tris-HCl buffer (50 mM, pH 8.0) containing 1 mM APS, 5 mM $MgCl_2$, 0.6 mM NADPH, 1 mM glucose-6-phosphate and 1 mM sodium pyrophosphate were added 5 U of glucose-6-phosphate dehydrogenase, 10 U of hexokinase, and 30 µL of ATP sulfurylase. The reaction was started by adding APS after the absorbance of NADH became constant. The decrease in NADPH absorbance at 340 nm was measured to determine the activity of ATP sulfurylase. One unit of the enzyme activity is defined as 1 µmole of product formed per minute, and the amount of protein was determined by the Coomasie Plus kit (Pierce Co.).

Chondroitin 6-Sulfate

The chondroitin sulfate chains are hybrid sequences containing 4,6-sulfated GalNAc-GlcUA disaccharide units. The enzymatic sulfation with sulfotransferases occurs on either the 4- or the 6-position, or both, of the GalNAc moiety using PAPS as a donor. Chondroitin sulfotransferases have been found from various sources including hen oviduct, [Suzuki et al., Biochim. Biophys. Acta, 50:16913 (1961); embryonic chick cartilage, [Robinson, Biochem. J., 113:543 (1969); Kimata et al., Mol. Cell. Biochem. 1:211 (1973); Silbert, J. Biol. Chem., 239:1310 (1964); Kim et al., J. Biol. Chem., 252:8292 (1977); Habuchi et al., Biochim. Biophys. Acta, 208:6161 (1980); Habuchi et al., Biochim. Biophys. Acta, 414:717 (1982)]; squid cartilage, [Habuchi et al., J. Biol. Chem., 246:7357 (1971)]; quail oviduct [Nakanishi et al., J. Biol. Chem., 256:544321 (1981) and mouse mast cell; [Sugumaran et al., J. Biol. Chem., 261:12659 (1986)] but their activities (as pmol) are almost too low to be used in synthesis. It has been reported that unsulfated chondroitin can be sulfated efficiently by the sulfotransferases from chick embryo cartilage, and both 4- and 6-sulfotransferases have been isolated. Habuchi et al., J. Biol. Chem., 246:7357 (1971). In order to produce chondroitin sulfotransferases for synthesis, the enzyme chondroitin 6-sulfotransferase (EC 2.8.2.17) was isolated from chick embryo cartilage. Habuchi et al., J. Biol. Chem., 246:7357 (1971).

Isolation of Chondroitin 6-Sulfotransferase

The procedure is essentially the same as described previously in Habuchi et al., J. Biol. Chem., 246:7357 (1971). The epiphyseal cartilage of tibias and femur of 13–14-day-old chick embryos (450 eggs, about 110 g, wet) was homogenized by ultrasonication with 3 volume and 2 volume of Buffer A (0.02M Tris-HCl, pH 7.2, 10 percent glycerol, 0.01M 2-mercaptoethanol, 0.5 mM EDTA) and the other buffer containing 0.5 percent (w/v) Triton X-100 for one minute. The process was repeated for 15 times at an interval of one minute at 4° C., respectively. The homogenates were centrifuged at 17000×g for one hour at 4° C. to provide the supernatant that was subjected to Toyopearl 650M (anion-exchanger) column (5×42 cm) previously equilibrated with Buffer A. The column was first washed with one liter of Buffer A, and then eluted with a linear gradient between one liter of Buffer A and one liter of Buffer A containing 0.4M NaCl in the reservoir. The flow rate was 120 mL/hour, and fractions (18 mL/each) were collected.

After $^{35}$S-radioactivity assay, the active fractions 45–75 were combined and concentrated to 25–30 mL on Ultrafiltration YM-10 membrane (Amicon). The concentrated enzyme preparation was dialyzed against 10 vol of Buffer A for 8 hours and then centrifuged at 50000×g for one hour at 4° C. to provide the supernatant as an enzyme preparation.

Enzyme Radioactivity Assay

The incubation mixture contained 5 µmol of imidazole-HCl, pH=6.8, 0.2 µmol of dithiothreitol (DTT), 2.5 µg of protamine-HCl, 0.5 µmol of chondroitin-Na (as glucuronic acid), $^{35}$S-PAPS (about 0.65 nmol, 27×10$^5$ cpm) and 10 µL of enzyme preparation in a total of 100 µL. After incubation at 37° C. for 20 minutes, the reaction was stopped by heating in a boiling water-bath for one minute. Pronase E (0.2 mg) was added, and the mixture was incubated for 30 minutes at 37° C. The solution was adjusted to 300 µL, and 700 µL of 95 percent EtOH/1 percent KOAc/0.5 mM EDTA were added to precipitate chondroitin and its sulfate. After 30 minutes in an ice-bath, the precipitates formed were collected by centrifugation at 15000 rpm for 10 minutes at 4° C. This procedure was repeated for three times. The final precipitates were dissolved in 50 µL of distilled water, and a 10 µL portion was taken and counted by liquid scintillation in Clear-sol I. The remaining 40 µL solution was hydrolyzed with chontroitinase ABC in a total 80 µL solution for 30 minutes at 37° C. A 10 µL portion was taken and chromatographed on Whatman paper No. 1 using BuOH: AcOH: NH40H (1N)=2:3:1 for 16 hours. The regions corresponding to the 4-sulfate (Rf=0.3) and 6-sulfate (0.23) were cut out and counted by liquid scintillation in 10 mL of Clear-sol I.

Calculation of Total Radioactivity

The 5000 chicken embryos were divided into 12 portions, treated as discussed above, and the enzymes were separated by the column chromatography as also described above. A total of 350 mL of the enzyme preparation was obtained. For the activity assay, 1 µL of the preparation and about 1.3 nmol (about 54×10$^5$ cpm) of $^{35}$S-PAPS were mixed in a total 100 µL of reaction mixture to give about 105 cpm.

1 µL of $^{35}$S-PAPS (0.44 nmol) gave about 18×10$^5$ cpm in 10 mL Clear-sol I.

The activity from 5000 chicken embryos that gave 350 mL of enzyme preparation:

350 mL×1000×105 cpm×0.44 nmol/18×105 cpm/20 minutes=0.42 units (1U=1 nmol/minute)

Protein amount in total 350 mL of enzyme preparation and specific activity

Cold acetone was added to 200 µL of this sulfotransferase preparation to 50 percent (v/v) concentration. After 30 minutes in an ice-bath, the mixture was centrifuged to provide 5 mg protein (dry weight). The total protein amount from 350 mL of preparation was 8.75 g. The specific activity of this preparation was 45.7 pmol/min/mg.

Cyclic Chondroitin 6-Sulfotransferase Reaction

A contemplated process for the formation of chondroitin 6-sulfate is shown schematically below in Scheme 4. This scheme is similar in concept to that of Scheme 2, but enumerates the sulfotransferase, the substrate and product structures, and the intermediate phosphorylated adenosine compounds that are cycled, but omits the remaining enzymes, sulfate and cofactors for added clarity.

Scheme 4

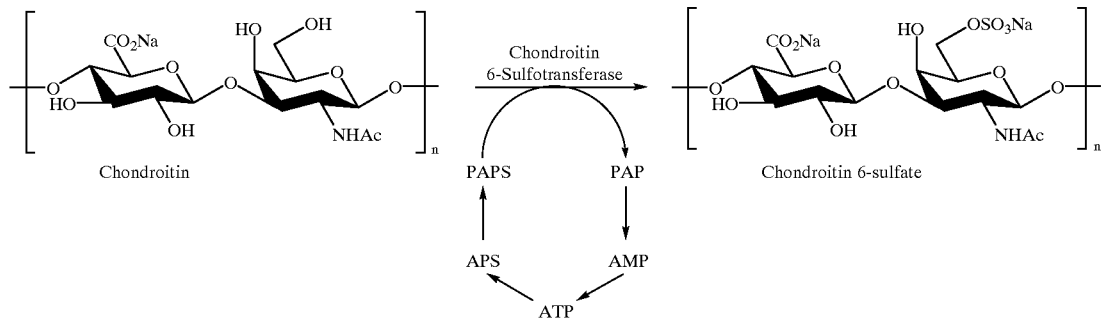

Hydroxysteroid sulfotransferase and its reaction

Hydroxysteroid sulfotransferases are mainly responsible for the metabolism of steroids. In the liver, steroid sulfation has been suggested to be a biochemical process resulting in the eventual excretion of the steroid sulfate formed in that tissue. Radominska et al., *Biochem. J.*, 272:597 (1990); Lee et al., *J. Biol. Chem.*, 269:15838 (1994).

The hydroxysteroid sulfotransferase (HSSTase) from rat liver transfers the sulfate group from PAPS to 3β-hydroxy-5-androsten-17-one (dehydroepianhyrostone; DHA). The purified enzyme was also found to transfer the sulfate group to several other hydroxysteroids, such as estradiol, testosterone, and androstenediol. The reaction was competitively inhibited by both reaction products, DHA 3-sulfate, and PAP. Marcus et al., *Anal. Biochem.*, 107:296 (1980). The sequence of this enzyme is reported in Ogura et al., *Biochem. Biophys. Res. Comm.*, 264:17615 (1989). A secretion vector harboring the gene encoding the catalytic domain of the HSSTase was constructed for overexpression in *E. coli*.

An important observation that is critical for the regeneration of PAPS from PAP is that PAP can be cleaved at its 3'-phosphate catalyzed by 3'-nucleotidase. The AMP generated can therefore be phosphorylated to ATP in the presence of pyruvate kinase and phospho(enol)pyruvate (PEP), as shown in Scheme 2. This PAPS regeneration system lessens the problems of high cost and instability of PAPS, and reduces the inhibition caused by PAPS and PAP. With this PAPS regeneration available, the multienzyme synthesis of DHA 3-sulfate was accomplished on mmol scales.

Dephosphorylation of PAP by 3'-nucleotidase

3'-Nucleotidase has been found here to catalyze the 3'-phosphate cleavage of PAP to AMP, in addition to its natural reaction; i.e., the hydrolysis of adenosine 3'-monophosphate. Although PAPS was also accepted by 3'-nucleotidase at a relatively lower rate, the dephosphorylated product adenosine 5'-phosphosulfate (APS) can be converted back to PAPS catalyzed by APS kinase. The dephosphorylation of PAPS can therefore be avoided if a limited amount of 3-nucleotidase is used.

Synthesis of DHA 3-sulfate by the enzymatic reaction

For enzymatic sulfation, the sulfated DHA was obtained either when HSSTase was used with isolated PAPS or in combination with the PAPS generating enzymes (ATP sulfurylase-and APS kinase), or with the contemplated cyclic PAPS regeneration system as in Scheme 2. The detailed procedure follows.

This product was clearly distinguished from its starting material by TLC with $CHCl_3$:MeOH (4:1) (Rf=0.34) and also characterized with $^1H$ and $^{13}C$ NMR. The spectra were identical with those of an authentic sample (Aldrich Co.). The observed mass (367) is in accord with the calculated mass for ($C_{19}H_{27}O_5S$)

Cloning of Hydroxysteroid Sulfotransferase from Rat Liver in *E. coli*

Reagents

All the chemicals were purchased from commercial sources as molecular biology grade reagents. Enzymes such as hexokinase, phosphoglucomutase and inorganic pyrophosphatase were purchased from Sigma Chemical Co. The total RNA of rat liver was purchased from Clonetech (Palo Alto, Calif.). The vector pFlag-1 was purchased from International Biotech. Inc. (New Haven, Conn.).

Microorganisms

The host strain *E. coli* XL1-Blue was obtained from Stratagene Co. (San Diego, Calif.). The microorganism was maintained on LB (Luria-Bertani) medium. When the host strain harbored a plasmid, LB medium containing 100 μg/mL of ampicillin was used. Stock culture was kept as cell suspension at −70° C. in 20 percent glycerol solution.

DNA manipulation

The RNA from rat liver was used as template for cDNA synthesis without mRNA purification by using oligo(dT)$_{10}$ as primer (Riboclone cDNA synthesis system from Promega Co., Wis.). In the typical 25 μL transcription reaction, 5 μg of RNA were annealed with 500 ng of oligo(dT)$_{10}$ at 70° C. for three minutes. Subsequently, the mixture was adjusted to contain 1 mM of dNTPs, 50 mM Tris-HCl, pH 8.3, 75 mM KCl, 10 mM $MgCl_2$, 0.5 mM spermidine, 10 mM DTT, 4 mM sodium pyrophosphate, 1 U RNasin ribonuclease inhibitor and 10–15 U AMV reverse transcriptase. The reaction was carried out at 42° C. for one hour and the reaction mixture heated at 94° C. for five minutes to inactivate the enzyme. The volume was then brought up to 50 μL by addition of 25 μL of DEPC-treated water and used for PCR amplifications. The vector pFlag-1 was transformed into *E. coli* XL1-Blue strain and prepared as described in Sambrook et al., *Molecular Cloning*, 2nd ed.; Cold Spring Harbor Laboratory, New York, 1989.

Amplification of the hydroxysteroid sulfotransferase gene from rat liver cDNA

Figure 3:
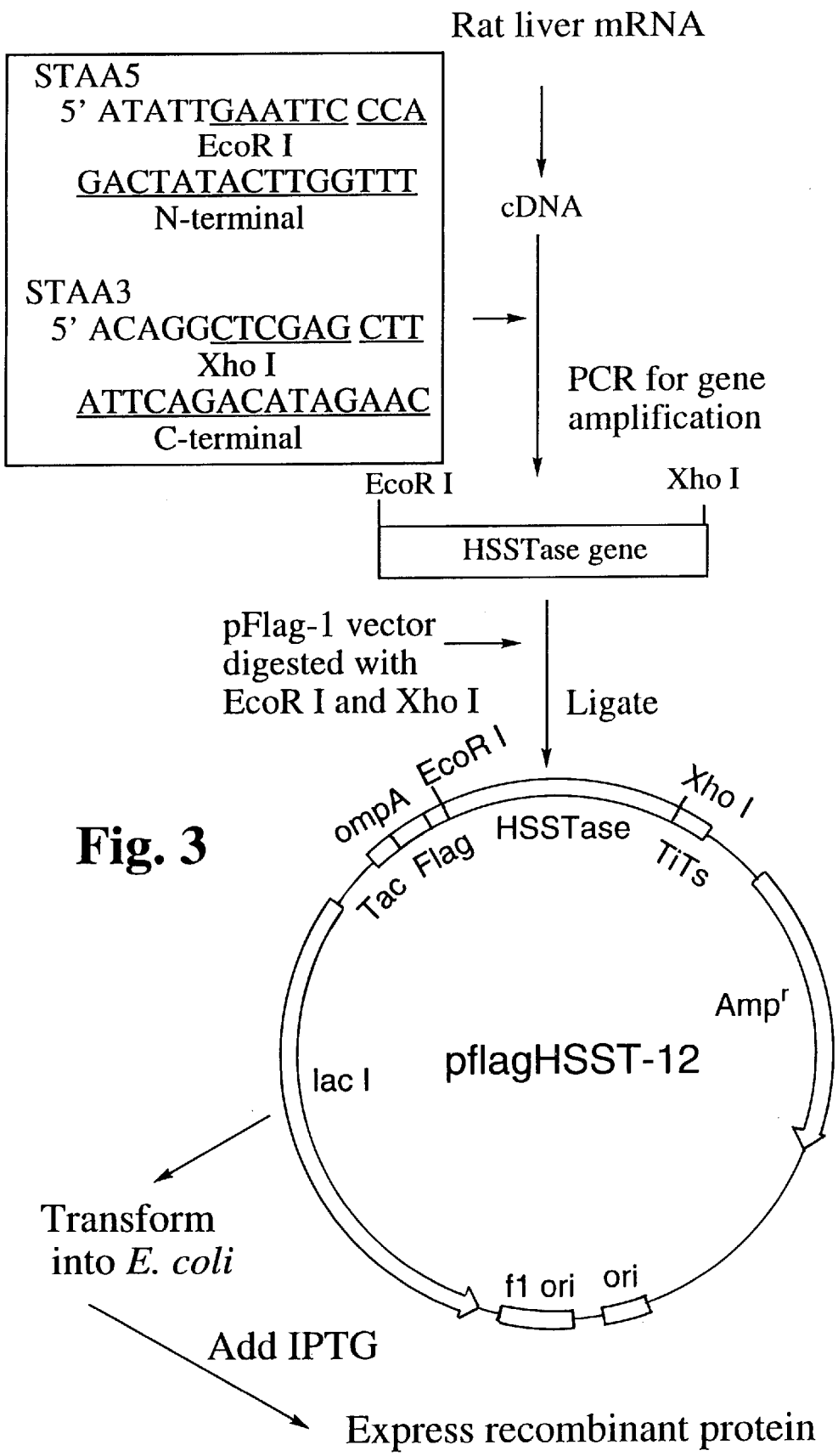
FIG. 3 is a schematic representation similar to those of FIGS. 1 and 2 that shows steps in the preparation of hydroxysteroid sulfotransferase (HSSTase). Here, rat liver mRNA was the starting material that was converted into cDNA and subjected to PCR amplification using primers STAA5 and STAA3 (SEQ ID NOs: 5 and 6, respectively) that contain EcoR I and Xho I restriction sites, respectively. Digestion of the amplified cDNA with those two enzymes provided an EcoR I-Xho I fragment that was ligated into vector pFlag-1 that was also digested with those enzymes to form vector pflagHSST-12. Transformation of *E. coli* with that vector followed by IPTG induction led to expression of the desired recombinant HSSTase that was used herein.

PCR amplification was performed in a 100 μL reaction mixture containing 3 μL of reverse transcription product, 400 nmol of primers STAA5 and STAA3 (custom synthesized from commercial sources, as illustrated in FIG. 3 and SEQ ID NOs: 5 and 6, respectively), 200 μM of different dNTPs, 50 mM KCl, 10 mM Tris-HCl (pH 8.3), 2 mM $MgCl_2$, 0.01 percent Triton X-100, and 2 units of *Thermus aquaticus* DNA polymerase. The reaction was overlayed with mineral oil and subjected to 35 cycles of amplifications. The cycle conditions were set as follows: denaturation, 94° C. for one minute; annealing, 55° C. for two minutes; and elongation, 72° C. for 1.5 minutes.

Construction of hydroxysteroid sulfotransferase expression vector

The DNA obtained from PCR amplification was extracted with phenol/chloroform and precipitated with ethanol at −70° C. for 30 minutes. The precipitated DNA was centrifuged and washed with 70 percent ethanol. The DNA pellet (about 500 μg) was then dissolved in a restriction enzyme buffer (H buffer from Boehringer Mannheim Biochemical Co.) and digested with EcoRI and Xho I (20 U each) at 37° C. for two hours.

The digested DNA was then recovered by phenol/chloroform extraction and ethanol precipitation (70 percent of final ethanol concentration containing 10 percent 3N sodium acetate, pH 5.2). This DNA was redissolved in 50 μL of TE buffer (pH 7.7) and purified on 0.7 percent agarose gel. The DNA band corresponding to 0.9 kb was separated from agarose gel and purified with Gene Clean kit (Bio-101 Co., San Diego). This DNA was used as insert.

The vector was also prepared from the digestion of pFlag-1 DNA (50 μg) with 20 U of EcoRI and Xho I and recovered with ethanol precipitation after extraction by phenol/chloroform. The vector was then further purified by agarose gel as described in the insert preparation. The insert was then ligated with the cut vector. Sambrook et al., *Molecular Cloning*, 2nd ed.; Cold Spring Harbor Laboratory, New York, 1989. The ligated DNA was then transformed into *E. coli* MF' strain (Stratagene Co., San Diego) and plated on LB agar plate containing 100 μg/mL ampicillin.

Screening for positive clones

Because the host strain *E. coli* does not contain the hydroxysteroid sulfotransferase gene, only the positive clones that contain this gene exhibited the PCR amplification product of 0.9 kb size when primers STAA5 and STAA3 were used. Therefore, the PCR method was used for screening. Forty colonies were randomly selected from plates and lysed with 50 μL of cell lysing buffer (20 mM Tris-HCl containing 1 percent Triton X-100 and 2 mM EDTA, pH 8.5). After boiling in water for 5 minutes and cooling, the cooled solution was used as a DNA template source for PCR amplification. The PCR amplification was the same as described in the amplification of hydroxysteroid sulfotransferase gene except 3 μL of cell lysing solution was used to replace the reverse transcription product. Three positive 10 clones were identified. One clone that gave the most intense PCR amplification was selected. The resulting hydroxysteroid sulfotransferase expression vector is shown in FIG. 3.

Preparation of the enzyme from the cloned strain Bacteria were grown on M9-CA medium ($Na_2HPO_4 \cdot 7H_2O$, 12.8 g; $KH_2PO_4$, 3.0 g; NaCl, 0.5 g; $NH_4Cl$, 1.0 g; in 1 L of deionized water) containing 1 mM $CaCl_2$ and 250 μL ampicillin to mid-logarithmic phase ($OD_{600}$ 0.5–0.6) at 37° C. and then induced with 0.005 mM IPTG for 10 hours at 30° C. with shaking. The culture from 2 L of grown *E. coli* cells were centrifuged at 9000 g for 25 minutes. Cells were homogenized in a solution of C buffer: 10 mM Tris-HCl (pH 7.5), 0.25M sucrose, 1 mM phenylmethylsulfonyl fluoride and 10 percent glycerol (v/v). These cells were then disrupted with a W385 Sonicator (Heat system-Ultrasonics, Farmingdale, N.Y.) and its microtip probe for three periods for 30 seconds each (2-s cycle pulses at 10 percent power output), interspersed by cooling for 30 seconds in an ice-salt bath. Chen, et al., *Protein Expression Purification* 1992, 3, 421. By centrifugation at 10,000 g for five minutes, the supernatant was collected as crude enzyme for synthetic purpose.

Enzyme assay

Standard assays of the HSSTase activities toward DHA were performed in a final volume of 1 mL of C buffer containing the substrate (100 nmol) dissolved in dimethyl sulfoxide (DMSO, 50 μL), PAPS (120 nmol), and the enzyme solution. Enzymatic reactions were started by addition of the substrate solutions, and the mixtures were incubated for one hour at 37° C. The sulfate esters formed were extracted as hydrophobic methylene blue complexes with chloroform and the absorbance at 651 nm was measured as described previously. Nose et al., *J. Biol. Chem.*, 233:1348 (1958); Ogura et al., *Molecular Pharmacol.*, 27:848 (1990).

Enzymatic synthesis of DHA 3-sulfate with ATP sulfurylase and APS kinase

The enzymatic reaction proceeded at 25° C. in 1 mL of C buffer containing 20 mM KCl, 40 mM $Na_2SO_4$, 5 mM $MgCl_2$, 1 U of ATP sulfurylase, 3.5 U of APS kinase, 2 U of inorganic pyrophosphatase, 20 U of pyruvate kinase, 100 μL of HSSTase, 2 mM ATP, 2 mM PEP, 1.5 mM DHA, and 2.5 percent DMSO. The product was detected by TLC with $CHCl_3$: MeOH (4:1) and the p-anisaldehyde stain solution. The reaction was run for one day and then extracted with $CHCl_3$. The collected organic layer was washed with water to remove DMSO and dried over $MgSO_4$. The resulting solution was concentrated and applied to column chromatography with $CHCl_3$:MeOH (5:1) to give the desired product.

Enzymatic synthesis of DHA 3-sulfate with PAPS regeneration system

The synthesis proceeded at 25° C. in 1 mL of C buffer containing 20 mM KCl, 40 mM $Na_2SO_4$, 5 mM $MgCl_2$, 1 U of ATP sulfurylase, 3.5 U of APS kinase, 2 U of inorganic pyrophosphatase,. 20 U of pyruvate kinase, 100 μL of HSSTase, 0.2 U of 3'-nucleotidase, 0.2 mM ATP, 2 mM phospho(enol)pyruvate, 1.5 mM DHA, and 2.5 percent DMSO. The remaining procedure was the same as described above. This reaction is shown schematically in Scheme 5, below, and is shown as was Scheme 4.

Scheme 5

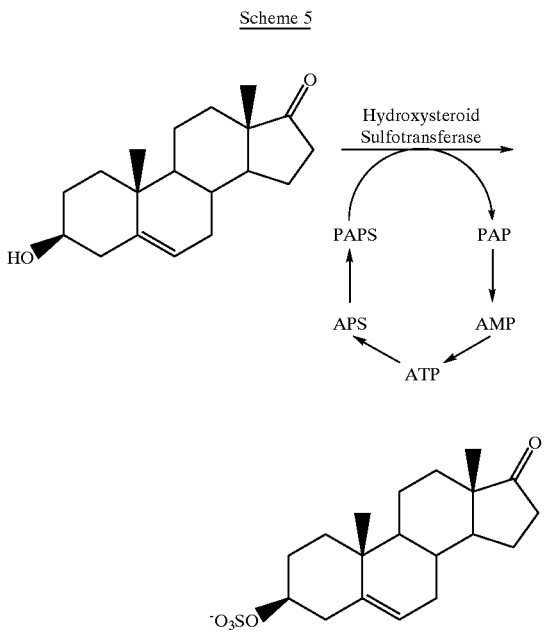

Nod Factor Sulfotransferase and Its Reaction

The roles of many oligo- and polysaccharides become more obvious and important after they are sulfated. A particular example comes from the molecular signal exchange of the Rhizobium-legume symbiosis. [Fisher et al., *Nature*, 357:655 (1992); Roche et al., *Cell*, 67:1131 (1991)]. The host legume releases signal to stimulate the coordinate expression of bacterial genes (nod genes) that are required for root nodulation of the legume.

These nod genes encode enzymes involved in the synthesis of Nod factors. So far, all the Nod factors from *Rhizobium meliloti* have been determined as β-1,4-N-acetyl-D-glucosamine oligosaccharides with various N-linked fatty acyl groups on the nonreducing end, rather than the N-acetyl group. Another feature is the exclusive sulfation at 6-OH on the reducing terminal. [LeRouge et al., *Nature*, 344:781 (1990); Faucher et al., *Mol.Plant-Microbe Interactions*, 2:291 (1989); Faucher et al., *J. Bacteriol.*, 170:5489 (1988); Atkinson et al., *Proc. Natl. Acad. Sci., USA*, 91:8418 (1994); Schroedock et al., *Mol. Plant-Microbe Interactions*,2:291 (1989); Cevantes et al., *Mol. Microbiol.*, 3, 745 (1989)] The gene of this enzyme responsible for such sulfation was determined to be NodH sulfotransferase (NodHST) and its sequence was elucidated. [Roche et al., *Cell*,67:1131 (1991)]. The discussion that follows is the first report of the purification and study of this enzyme.

Reagents

The plasmid pKEN2 was obtained from Professor G. L. Verdine (Department of Chemistry, Harvard University, Cambridge, Mass. 02138). Protein contents were measured using the BCA protein assay kit (Pierce Co.). All the chemicals were purchased from commercial sources as molecular biology grade reagents.

Microorganisms

The microorganism, *Rhizobium meliloti* containing Nod factor sulfotransferase (NodHST) gene was obtained from ATCC (ATCC 10310). The host strain *E. coli* BL21(DE3) were purchased from Novogen and were grown in LB (Laria-Bertani) medium. The *E. coli* BL21(DE3) containing plasmid derived from pKEN2 were grown in LB or SOB medium containing 10 mM $MgCl_2$ and 250 mg/mL ampi-cillin. Stock cultures were kept at $-70°$ C. in 20 percent glycerol solution.

DNA manipulation and PCR amplification of the NodH gene

Figure 4:
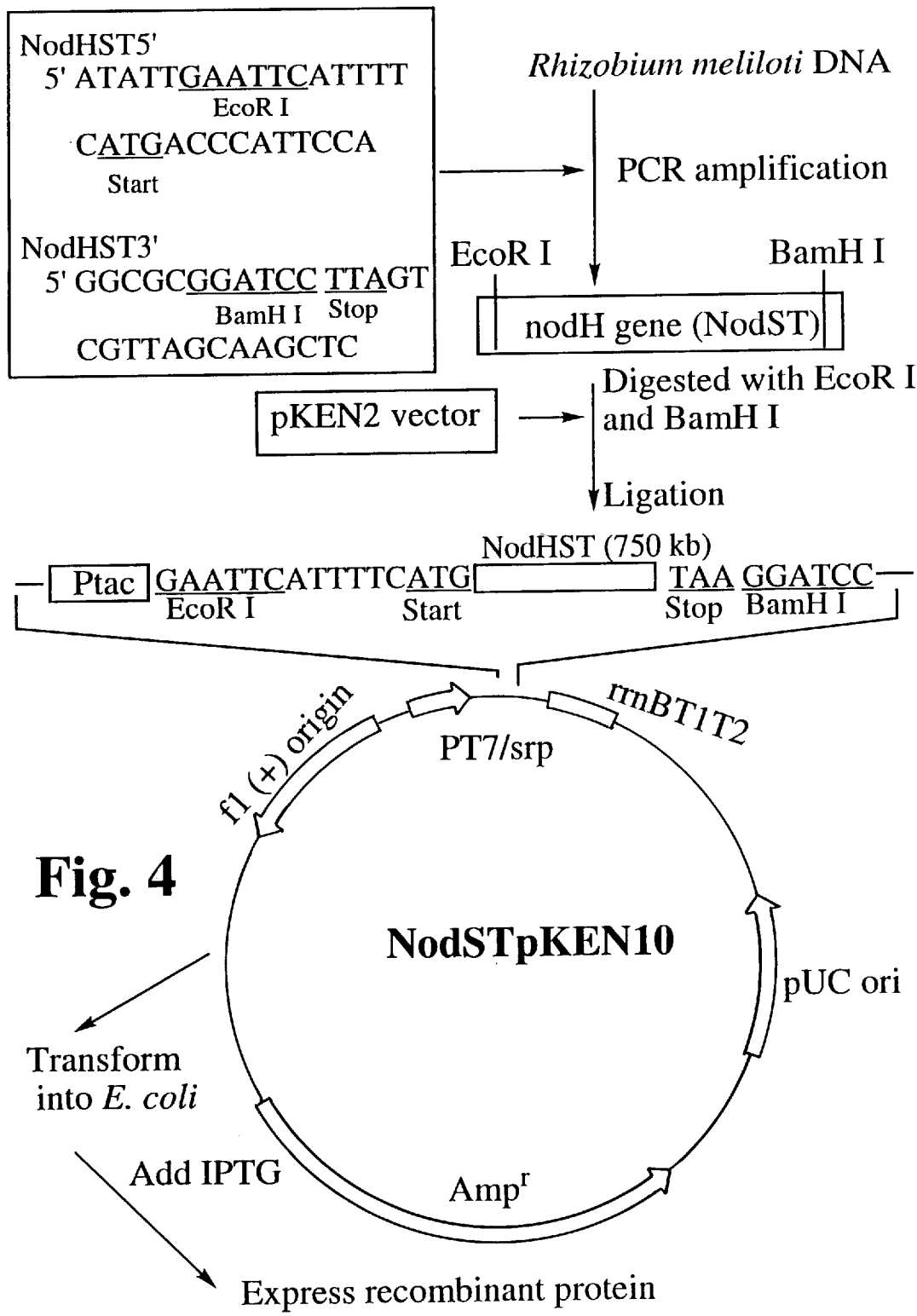
FIG. 4 is another schematic representation similar to those of FIGS. 1–3 that shows steps in the preparation of Nod factor sulfotransferase (NodHSST). Here, DNA from *Rhizobium meliloti* was subjected to PCR amplification using primers NodHST5' and NodHST3' (SEQ ID NOs: 7 and 8, respectively) that contained EcoR I and BamH I restriction sites, respectively. Digestion of the amplified cDNA with these two enzymes provided an EcoR I-BamHI fragment that was ligated into vector pKEN2 that was also digested with those enzymes to form vector NodSTpKEN10. Transformation of *E. coli* with that vector followed by IPTG induction led to expression of the desired NodHST that was used herein.

The cells of *Rhizobium meliloti* were suspended directly in cell lysing buffer (20 mM Tris-HCl, 1 percent Triton, and 20 mM EDTA; pH 8.5). After boiling in water for 5 minutes, the lysed cell solution was used as the DNA source for PCR amplification. The primers were designed to contain BamH I and EcoR I restriction sites and several extra bases as spacers between the ribosome binding site and start codons to maximize the expression (FIG. 4). PCR amplification was performed in a 100 mL reaction mixture containing 3 mL of *R. meliloti* cell lysing solution, 400 nmole each of primers NodST5' (SEQ ID NO:7) and NodST3' (SEQ ID NO:8), 200 mM of different dNTPs, 50 mM KCl, 10 mM Tris-HCl (pH 8.3), 2 mM $MgCl_2$, 0.01 percent gelatin, 0.1 percent TritonX100 and 2 U of *Thermus aquaticus* DNA polymerase. The reaction was overlayed with 100 mL of mineral oil and subjected to 35 cycles of amplification. The cycle conditions were set as denaturation at $94°$ C. for 1 minute, annealing at $55°$ C. for 1.5 minutes and elongation at $72°$ C. for 1.5 minutes.

Construction of NodST expression vector

The DNA obtained from PCR was precipitated in 70 percent ethanol and purified on a 0.8 percent agarose gel. The DNA band conrresponding to 0.7 kb was separated and purified with Geneclean II kit obtained from Bio 101 (La Jolla, Calif.). The DNA was then dissolved in restriction enzyme buffer H (Boehringer Mannhein Biochemical Co.) and digested with BamH I and EcoR I (20 U/mg DNA) at $37°$ C. for 2 hours. The digested DNA was then recovered by treatment with Strataclean resin obtained from Stratagene Co. (San Diego, Calif.) followed by ethanol precipitation, and resuspened in TE buffer (pH 7.7).

The plasmid pKEN2 was also digested with BamH I and EcoR I under the same conditions as the PCR insert. The digested NodHST gene insert and PKEN vector were then ligated and transformed into *E. coli* BL21 (DE3). The transformed cells were plated onto LB agar plates containing 250 mg/mL ampicillin.

Screening for positive clones

Because *E. coli* did not contain NodHST, direct PCR amplification of DNA of the transformed colonies by using NodST5' and NodST3' primers provided an efficient way to identify the positive clones. Out of 20 colonies randomly selected that were used for PCR as described previousely, the colony that provided the most intense band corresponding with the NodHST gene size was selected for further investigation and designated as NodHST10. The plasmid of that colony was designated as NodSTpKEN10. The existence of the desired insert was further confirmed by digesting NodSTpKEN10 with the two restriction enzymes (BamH I and EcoR I).

Overexpression of NodHST enzyme

Cloned NodHST gene in pKEN2 vector was controlled by a T7 promotor and is expressed with T7 RNA polymerase. The host cell *E. coli* BL21 (DE3) contains T7 RNA polymerase gene and can be induced by the addition of IPTG (*Methods in Enzymology*, Vol 185, p.61–89) A colony from LB plate containing 250 mg/mL ampicillin was picked and grown on 2 L of LB medium containing 250 mg/mL ampicillin. When the cell density reached $OD_{600}=0.4$ at $37°$ C., IPTG was added to an optimized final concentration of 0.5 mM. It was found the maximum yield of enzyme can be obtained in a 13 hour incubation of the culture at $30°$ C. after induction of IPTG. The expression level of the target protein was analyzed by SDS-PAGE using Pharm System (Pharmacia Co.) with a 10–15 percent gradient of polyacrylamide. The culture broth was centrifuged (9,000×g, 25 min, 4° C.) and then suspended in 40 mL of Tris-HCl buffer (50 mM, pH 7.5). After lysing cells using French Press (15,000 psi), debris was removed by centrifugation at 4° C. (16,000×g for 45 minutes), and the supernatant was collected. The crude cell extracts were used in the synthetic studies of sulfation discussed below.

Enzymatic reaction of NodHST

The synthesis was carried out at 25° C. in 1 mL of Tris-HCl (100 mM, pH 7.5) containing 20 mM $MgCl_2$, 2 mM N,N',N"-triacetylchitotriose (or N,N'-diacetylchitobiose), 2 mM 3'-phosphoadenosine-5'-phosphosulfate (PAPS), and 200 mL of cell extract from above. The product was detected by TLC with $CH_3Cl_3$/MeOH/AcOH/$H_2O$ (25:15:2:1) and the p-anisaldehyde stain solution. Both the disaccharide and trisaccharide were accepted by enzyme as substrates, and the products were obviously different from the starting material by TLC with $CH_3Cl_3$/MeOH/AcOH/$H_2O$ (25:15:2:1). These reactions are shown schematically below in Scheme 6.

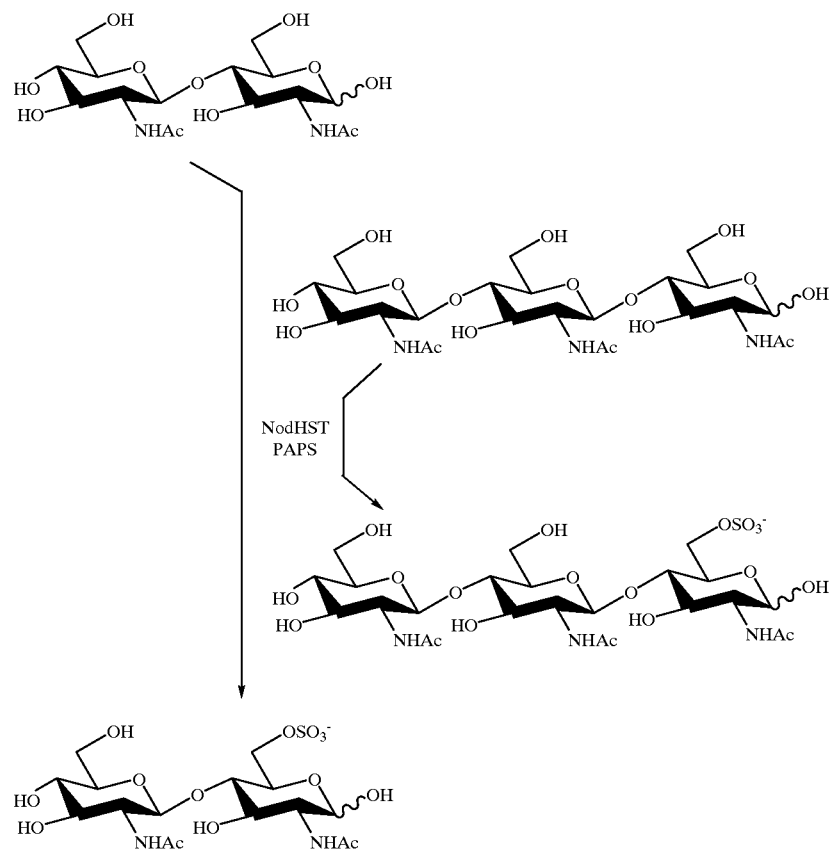

Scheme 6

The foregoing description and the examples are intended as illustrative and are not to be taken as limiting. Still other variations within the spirit and scope of this invention are possible and will readily present themselves to those skilled in the art.

We claim:

1. A process for using 3'-phosphoadenine-5'-phosphosulfate (PAPS) in an enzyme-catalyzed sulfation of an acceptor with recycling of phosphorylated adenosine intermediates that comprises the steps of:
   (a) admixing the following ingredients in an aqueous medium containing magnesium and potassium ions within a single vessel to form an aqueous reaction medium
      (i) 3'-nucleotidase or 3'(2'),5'-bisphosphate nucleotidase;
      (ii) ATP sulfurylase;
      (iii) APS kinase;
      (iv) pyrophosphorylase;
      (v) a sulfotransferase;
      (vi) at least one adenine-containing compound selected from the group consisting of ATP, ADP, AMP, APS, PAPS and PAP;
      (vii) sulfate ion;
      (viii) an ATP-regenerating system comprising a phosphate donor and a phosphorylating enzyme; and
      (ix) a sulfate acceptor for said sulfotransferase
   the concentration of said sulfate ion being greater than the concentration of all of said adenine-containing compound, and the activity of said 3'-nucleotidase being less than that of the enzymes of (ii)–(v); and
   maintaining said aqueous reaction medium at a pH value of about 5 to about 10 at a temperature of about zero degrees C to about 40° C. for a time period sufficient for said acceptor to be sulfated.

2. The process according to claim 1 including the further step of recovering the sulfated acceptor.

3. The process according to claim 1 wherein said ATP-regenerating system comprises myokinase, pyruvate kinase and phospho(enol)pyruvate.

4. The process according to claim 1 wherein said sulfotransferase is chondroitin transferase.

5. The process according to claim 1 wherein said sulfotransferase is hydroxysteroid sulfotransferase.

6. The process according to claim 1 wherein said sulfotransferase is NodH sulfotransferase.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:1:

ATATTGAGCT CGATCAAATA CGACTTACTC ACCTG                                35

(2) INFORMATION FOR SEQ ID NO:2:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:2:

GCGCAAGCTT TTATTATTTA TCCCCCAGCA AATC                                 34

(2) INFORMATION FOR SEQ ID NO:3:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

ATATTGAGCT CGCGCTGCAT GACGAAAAC                                       29

(2) INFORMATION FOR SEQ ID NO:4:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

GCGCAAGCTT TTATTAGGAT CTGATAATAT CGTT                                 34

(2) INFORMATION FOR SEQ ID NO:5:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

ATATTGAATT CCCAGACTAT ACTTGGTTT                                       29

(2) INFORMATION FOR SEQ ID NO:6:

(i) SEQUENCE CHARACTERISTICS:
            (A) LENGTH: 29 base pairs
            (B) TYPE: nucleic acid
            (C) STRANDEDNESS: single

```
            (D) TOPOLOGY: linear (ii) MOLECULE TYPE: DNA (genomic)

(xi) SEQUENCE DESCRIPTION: SEQ ID NO:6:

ACAGGCTCGA GCTTATTCAG ACATAGAAC                                29

(2) INFORMATION FOR SEQ ID NO:7:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

ATATTGAATT CATTTTCATG ACCCATTCCA                                30

(2) INFORMATION FOR SEQ ID NO:8:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

GGCGCGGATC CTTAGTCGTT AGCAAGCTC                                 29
```